United States Patent [19]

Wade et al.

[11] 4,070,465
[45] Jan. 24, 1978

[54] VARIOUS 2-(SUBSTITUTED PIPERAZINYL)-1H-BENZ [DE]ISOQUINOLINE-1,3 (2H) -DIONES

[75] Inventors: Peter C. Wade, Pennington, N.J.; Berthold Richard Vogt, Yardley, Pa.

[73] Assignee: E. R. Squibb & Sons, Inc., Princeton, N.J.

[21] Appl. No.: 699,723

[22] Filed: June 24, 1976

[51] Int. Cl.$^2$ .................. A61K 31/495; C07D 401/06
[52] U.S. Cl. .............................. 424/250; 260/268 TR
[58] Field of Search .................. 260/260 TR; 424/250

[56] References Cited

U.S. PATENT DOCUMENTS

| | | | |
|---|---|---|---|
| 3,247,208 | 4/1966 | Schenkel | 260/281 |
| 3,560,495 | 2/1971 | Frankus et al. | 260/247.1 |
| 3,625,947 | 12/1971 | Noguchi et al. | 260/281 |
| 3,642,386 | 2/1972 | Cusic et al. | 260/281 |
| 3,770,763 | 11/1973 | Cusic et al. | 260/309 |
| 3,935,227 | 1/1976 | Wade et al. | 260/281 S |
| 3,947,452 | 3/1976 | Wade et al. | 260/281 NH |
| 3,959,286 | 5/1976 | Wade et al. | 260/281 NH |
| 3,996,362 | 12/1976 | Wade et al. | 424/258 |
| 3,996,363 | 12/1976 | Wade et al. | 424/258 |
| 4,006,238 | 2/1977 | Wade | 424/258 |
| 4,007,191 | 2/1977 | Wade et al. | 260/288 |

FOREIGN PATENT DOCUMENTS 2,167,355  8/1973  France ................................ 260/281

OTHER PUBLICATIONS

Kimura, et al., CA vol. 62, p. 11950c.

Primary Examiner—Donald G. Daus
Assistant Examiner—Jose Tovar
Attorney, Agent, or Firm—Lawrence S. Levinson; Merle J. Smith; Stephen B. Davis

[57] ABSTRACT

Compounds of the following formula and their acid addition salts

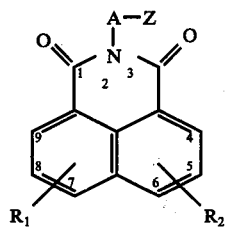

Z is

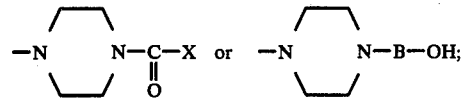

A is straight or branched chain alkylene of 2 to 6 carbons; B is straight chain alkylene of 2 to 4 carbons; X is straight or branched chain alkyl of 1 to 8 carbons, phenyl, benzyl, phenethyl, substituted phenyl, substituted benzyl, or substituted phenethyl, $R_1$ and $R_2$ are located at the 7 or 8 and 5 or 6 position respectively and are independently selected from the group consisting of hydrogen, straight or branched chain alkyl of 1 to 4 carbons, straight or branched chain alkoxy of 1 to 4 carbons, Cl, Br, F, amino, nitro, $CF_3$, and cyano; are disclosed. These compounds possess antiprotozoal activity.

11 Claims, No Drawings

VARIOUS 2-(SUBSTITUTED PIPERAZINYL)-1H-BENZ[DE]ISOQUINOLINE-1,3 (2H)-DIONES

BACKGROUND OF THE INVENTION

1H-Benz[de]isoquinoline-1,3(2H)-diones substituted in the 2-position by a (substituted-piperazinyl)alkyl group are disclosed as possessing antidepressant and anti-inflammatory activity in U.S. Pat. Nos. 3,940,397 and 3,940,398 of Wade et al. Other 2-substituted 1H-benz[de]isoquinoline-1,3(2H)-diones possessing antidepressant and anti-inflammatory activity are disclosed by Wade et al. in U.S. Pat. Nos. 3,935,227 and 3,947,452.

Various naphthalimide compounds have also been developed for use as dyes and optical brightening agents. Kimura et al., for example, at Chem. Abst., Vol. 62, 11950c, disclose N-[2-piperidinoethyl]-4-methoxy-1,8-naphthalimide (i.e. 6-methoxy-2-[2-(1-piperidinyl)ethyl]-1H-benz[de]isoquinoline-1,3(2H)-dione under the current Chem. Abst. nomenclature) as an optical brightening agent. Noguchi et al. in U.S. Pat. No. 3,625,947 disclose 2-[2-(2 or 4-pyridyl)ethyl[-1H-benz[de]isoquinoline-1,3(2H)-diones as fluorescent whitening agents.

Schenker et al. in U.S. Pat. No. 3,247,208 disclose that 1H-benz[de]isoquinoline-1,3(2H)-diones having a (1-substituted-4-piperidinyl) group in the 2-position possess anesthetic properties. Imides having a nitroimidazolyethyl group as an N-substituent and possessing anti-bacterial and anti-protozoal activity are disclosed in U.S. Pat. Nos. 3,642,836 and 3,770,763 to Cusic et al. Certain imido dicarboxylic acid imides possessing various pharmacological properties are disclosed in U.S. Pat. No. 3,560,495 to Frankus et al.

SUMMARY OF THE INVENTION

This invention relates to new 2-substituted-1H-benz[de]isoquinoline-1,3(2H)-diones and their acid addition salts of the formula

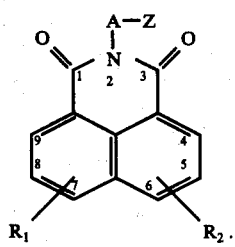

(I)

The symbols have the following meaning in formula I and throughout this specification.

$R_1$ and $R_2$ are located at 7 or 8 and 5 or 6 position respectively and are independently selected from hydrogen, straight or branched chain alkyl of 1 to 4 carbons, straight or branched chain alkoxy of 1 to 4 carbons, Cl, Br, F, amino, nitro, $CF_3$, and cyano.

A is straight or branched chain alkylene of 2 to 6 carbons.

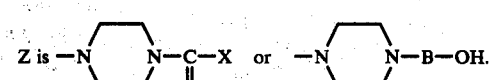

B is straight chain alkylene of 2 to 4 carbons.

X is straight or branched chain alkyl of 1 to 8 carbons, phenyl, benzyl, phenethyl, substituted phenyl, substituted benzyl, or substituted phenethyl.

DETAILED DESCRIPTION OF THE INVENTION

The straight or branched chain alkyl group of 1 to 4 or 1 to 8 carbons referred to throughout this specification include groups such as methyl, ethyl, n-propyl, i-propyl, n-butyl, t-butyl, etc. The straight or branched chain alkoxy groups of 1 to 4 carbons include such alkyl groups attached to an oxygen, e.g. methoxy, ethoxy, n-propoxy, etc.

Straight or branched chain alkylene of 2 to 6 carbons is intended to include groups such as —$(CH_2)_n$— wherein $n$ is 2 to 6,

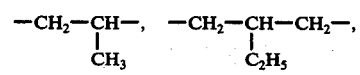

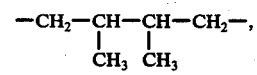

etc.

The term "substituted phenyl" refers to a phenyl ring having a single substituent selected from straight or branched alkyl of 1 to 4 carbons, straight or branched chain alkoxy of 1 to 4 carbons, Cl, Br, F, $CF_3$, and nitro, di(Cl), di(Br), di(methyl), di(methoxy), and tri(methoxy). Similarly, the terms "substituted benzyl" and "substituted phenethyl" include the same substituents on the phenyl ring.

Preferred embodiments of this invention are as follows:

A is straight or branched chain alkylene of 2 to 4 carbons.

$R_1$ and $R_2$ are independently selected from hydrogen, methyl, methoxy, Cl, and Br and F.

The most preferred compounds are:

$R_1$ and $R_2$ are both hydrogen.

A is straight chain alkylene of 2 to 4 carbons, especially —$CH_2$—$CH_2$—.

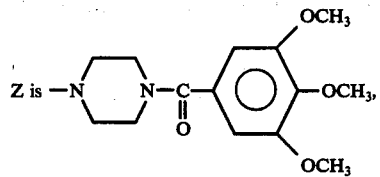

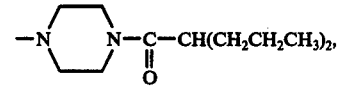

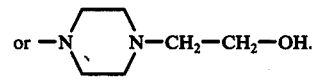

The new compounds of this invention wherein Z is

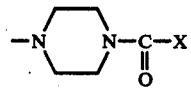

are prepared by acylating a naphthalimide of the formula

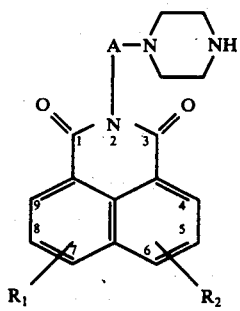

with an acid chloride of the formula

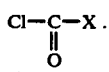

This reaction is preferably performed by refluxing for several hours in an inert solvent such as pyridine.

The intermediate of formula II can be prepared by reacting a naphthalic anhydride of the formula

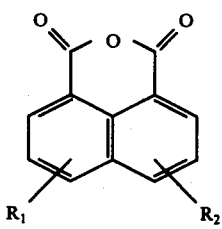

with an aminoalkylenepiperazine of the formula

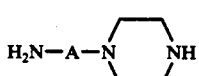

by refluxing for several hours in a suitable solvent such as water.

The new compounds of this invention wherein Z is

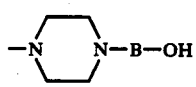

are preferably prepared by reacting a naphthalimide of the formula

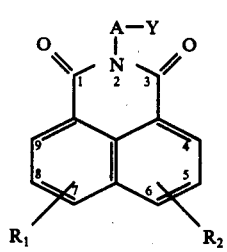

wherein $R_1$, $R_2$, and A are as defined above and Y is a leaving group such as tosylate, methane sulfonate or halogen, with a compound of the formula

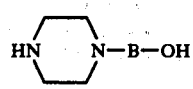

wherein B is as defined above. This reaction is performed in a nonreactive organic solvent such as benzene, toluene, pyridine, dimethylsulfoxide, etc., and with the optional presence of an organic base such as potassium carbonate. The reaction is performed by heating at about the reflux temperature for several hours.

The reactants of formulas II, III, IV, V, VI and VII are known in the art or are readily obtainable by known procedures as note the Wade et al. patents referred to above. Further process details are also provided in the illustrative examples.

The compounds of formula I wherein either or both $R_1$ and $R_2$ are amine are prepared by reducing the corresponding nitro substituted compound with a reducing agent such as hydrogen over a palladium catalyst or a suitable chemical reducing agent. This is preferably done as the last stage in the reaction procedures described above.

Depending on the reaction conditions and the starting materials used, the new compounds are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The compound of formula I possess useful antiprotozoal activity. For example, they inhibit the growth of the protozoa organism *Trichomonas vaginalis*. Thus, a compound or mixture of compounds of formula I or a pharmaceutically acceptable salt thereof can be orally administered to various mammalian species to combat such protozoa infections in an amount ranging from about 10 to about 100 mg. per kg. per day. For such purpose the compound or mixture of compounds can be formulated with a conventional excipient, vehicle, binder, preservative, etc., as called for by accepted pharmaceutical practice.

Also, the compounds of formula I wherein Z is

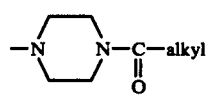

in addition to their anti-protozoal activity have activity against the organism *Staphylococcus aureus*. Thus, these compounds can also be used to combat microbial infections caused by this microorganism.

The following examples are illustrative of the invention and represent preferred embodiments. Other modifications may be readily produced by suitable variations of the reactants. All temperatures are on the centigrade scale.

EXAMPLE 1

2-[2-[4-(2-Hydroxyethyl)-1-piperazinyl]ethyl]-1H-benz[de]-isoquinoline-1,3(2H)-dione, hydrochloride (1:2)

a. 2-(2-Hydroxyethyl)-1H-benz[de]isoquinoline-1,3(2H)-dione 50 g. (0.252 mole) of naphthalic anhydride and 16 g. (0.262 mole) of ethanolamine are refluxed for three hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°–173°.

b. 2-(2-Hydroxyethyl)-1H-benz[de]isoquinoline-1,3(2H)-dione, 4-methylbenzenesulfonate ester 52 g. (0.216 mole) of the 2-(2-hydroxyethyl)-1H-benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnight at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)-dione, 4-methylbenzenesulfonate ester.

c. 2-[2-[4-(2-Hydroxyethyl)-1-piperazinyl]ethyl]-1H-benz[de]isoquinoline-1,3(2H)-dione, hydrochloride (1:2)

30 g. (0.075 mole) of the 4-methylbenzenesulfonate ester from part (b), 10.8 g. (0.083 mole) of N-(β-hydroxyethyl)-piperazine, and 9.77 g. (0.075 mole) of diisopropylethylamine are refluxed in 500 ml. of toluene for one hour. The reaction mixture is cooled, washed with 10% KOH, filtered, and the aqueous layer is separated and washed four times with chloroform. The combined organic layers are washed with water and evaporated. The residue is recrystallized from alcohol and then toluene to yield 2-[2-[4-(2-hydroxyethyl)-1-piperazinyl]ethyl]-1H-benz[de]isoquinoline-1,3(2H)-dione; m.p. 165°–166°.

This free base is dissolved in hot alcohol and treated with ethanolic HCl to yield 18.7 of 2-[2-[4-(2-hydroxyethyl)-1-piperazinyl]ethyl]-1H-benz[de]-isoquinoline1,3(2H)-dione, hydrochloride (1:2); m.p. 289°–290° (dec.).

EXAMPLES 2-22

Following the procedure of example 1 but substituting for the N-(β-hydroxyethyl)-piperazine the piperazines shown below in Col. II and employing the substituted 4-methylbenzenesulfonate esters shown in Col. I, one obtains the final products shown in Col. III.

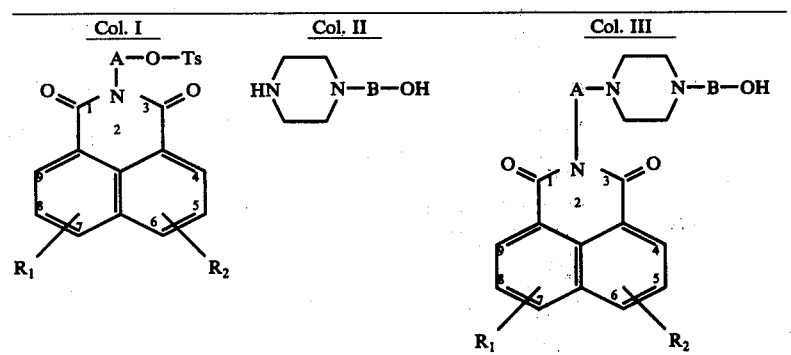

| Ex. | A | B | $R_1$ 7 | 8 | $R^2$ 5 | 6 |
|---|---|---|---|---|---|---|
| 4 | $-(CH_2)_3-$ | $-(CH_2)_2-$ | H | H | H | H |
| 5 | $-(CH_2)_2-$ | $-(CH_2)_3-$ | H | H | H | H |
| 6 | $-(CH_2)_3-$ | $-(CH_2)_2-$ | H | H | H | H |
| 7 | $-(CH_2)_6-$ | $-(CH_2)_2-$ | H | H | H | H |
| 8 | $-CH-CH_2-$<br>\|<br>$CH_3$ | $-(CH_2)_4-$ | H | H | H | H |
| 9 | $-CH_2-CH-CH_2-$<br>\|<br>$CH_3$ | $-(CH_2)_3-$ | H | H | H | H |
| 10 | $-CH-CH-CH_2-$<br>\| \|<br>$CH_3$ $CH_3$ | $-(CH_2)_2-$ | $CF_3$ | H | H | H |
| 11 | $-(CH_2)_2-$ | $-(CH_2)_4-$ | Cl | H | H | H |
| 12 | $-(CH_2)_3-$ | $-(CH_2)_2-$ | H | $-CH_3$ | H | H |
| 13 | $-(CH_2)_2-$ | $-(CH_2)_2-$ | $-OCH_3$ | H | H | H |
| 14 | $-CH-CH_2-$<br>\|<br>$CH_3$ | $-(CH_2)_4-$ | $-NO_2$ | H | H | H |
| 15 | $-CH_2-CH-CH_2-$<br>\|<br>$CH_3$ | $-(CH_2)_2-$ | $-CN$ | H | H | H |
| 16 | $-(CH_2)_2-$ | $-(CH_2)_3-$ | Cl | H | H | Cl |
| 17 | $-(CH_2)_3-$ | $-(CH_2)_4-$ | H | Br | H | H |
| 18 | $-(CH_2)_2-$ | $-(CH_2)_2-$ | $t\text{-}C_4H_9$ | H | H | H |
| 19 | $-(CH_2)_2-$ | $-(CH_2)_2-$ | H | $-OC_2H_5$ | H | H |
| 20 | $-(CH_2)_2-$ | $-(CH_2)_2-$ | $-CH_3$ | H | H | $-CH_3$ |
| 21 | $-CH-CH_2-$<br>\|<br>$CH_3$ | $-(CH_2)_2-$ | H | Cl | Cl | H |

-continued

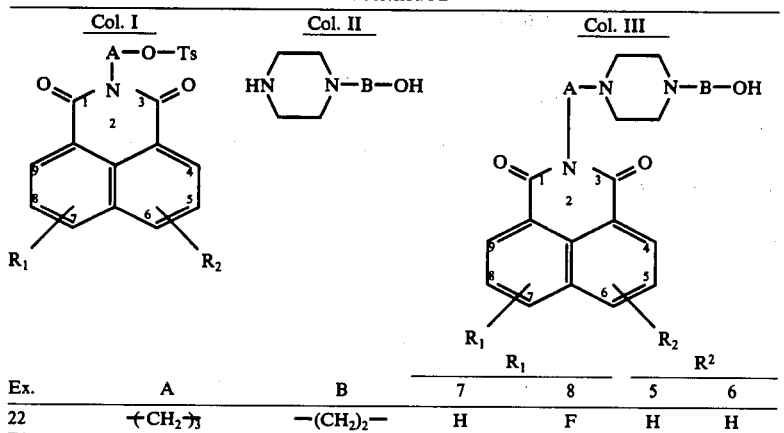

| Ex. | A | B | 7 | 8 | 5 | 6 |
|---|---|---|---|---|---|---|
| 22 | ₍CH₂₎₃ | —(CH₂)₂— | H | F | H | H |

EXAMPLE 23

2-[2-[4-(3,4,5-Trimethoxybenzoyl)-1-piperazinyl]ethyl]1H-benz[de]isoquinoline-1,3(2H)-dione, hydrochloride (1:1)

a. 2-[2-(1-Piperazinyl)ethyl]-1H-benz[de]isoquinoline-1,3(2H)-dione 49.5 g. (0.25 mole) of naphthalic anhydride and 32 g. (0.25 mole) of N-(2-aminoethyl)piperazine are refluxed for three hours in 200 ml. of water. The solution is allowed to cool and the insoluble product is filtered off and recrystallized from absolute ethanol to yield 30 g. of 2-[2-(1piperazinyl)ethyl]-1H-benz[de]isoquinoline-1,3-(2H)-dione.

b. 2-[2-[4-(3,4,5-Trimethoxybenzoyl)-1-piperazinyl]ethyl]1H-benz[de]isoquinoline-1,3(2H)-dione, hydrochloride (1:1)

8 g. (0.026 mole) of 2-[2-(1-piperazinyl)ethyl]-1H-benz[de]isoquinoline-1,3(2H)-dione from part (a) and 12.5 g. (0.054 mole) of 3,4,5-trimethoxybenzoylchloride are refluxed for two hours in 250 ml. of dry pyridine. The pyridine is evaporated and the residue is dissolved in chloroform. The chloroform is washed with 10% KOH and water and evaporated. The residue is dissolved in hot ethanol/dioxane, treated with ethanolic HCl and dried (80°) under vacuum to yield 7.4 g. of 2-[2-[4-(3,4,5-trimethoxybenzoyl)-1-piperazinyl]ethyl-1H-benz[de]isoquinoline-1,3(2H)-dione, hydrochloride (1:1); m.p. 263°-264° (dec.).

EXAMPLE 24

2-[2-[4-(1-Oxo-2-propylpentyl)-1-piperazinyl]ethyl]-1H-benz[de]isoquinoline-1,3(2H)-dione, hydrochloride (1:1)

8.0 g. (0.026 mole) of 2-[2-(1piperazinyl)ethyl]-1H-benz[de]isoquinoline-1,3(2H)-dione from example 23 (a) and 8.82 g. (0.054 mole) of dipropylacetylchloride are refluxed in 250 ml. of dry pyridine for two hours. The pyridine is evaporated and the residue is dissolved in chloroform and washed with 10% KOH and water. The chloroform is evaporated and the residual dark oil is stirred with ether overnight. After filtration of a small amount of residual material, 10 ml. of 5N ethanolic HCl is added to the mother liquor. The resulting precipitate is filtered off, recrystallized from isopropanol, and dried (80°) under a vacuum to yield 8.85 g. of 2-[2-[4-(1oxo-2-propylpentyl)-1-piperazinyl]ethyl]-1H-benz[de]-isoquinoline-1,3(2H)-dione, hydrochloride (1:1); m.p. 236°-237°.

EXAMPLES 25-43

Following the procedure of examples 23 and 24 but employing the 2-[(piperazinyl)alkyl]-1H-benz[de]-isoquinoline-1,3(2H)-dione shown in Col. I and the acid chloride shown in Col. II, one obtains the final compounds shown in Col. III.

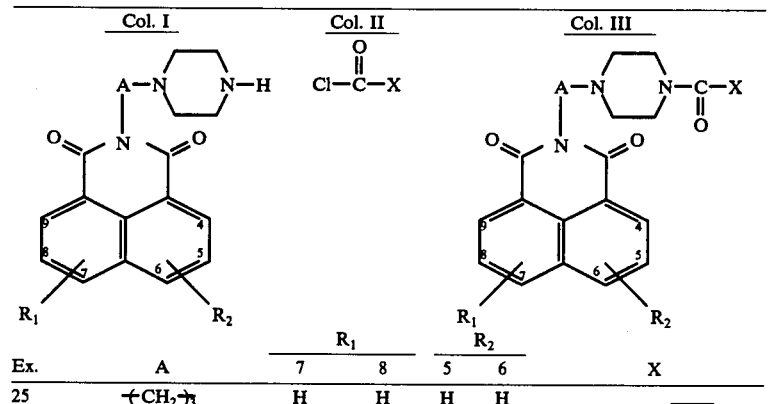

| Ex. | A | 7 | 8 | 5 | 6 | X |
|---|---|---|---|---|---|---|
| 25 | ₍CH₂₎₃ | H | H | H | H | —CH₂—⟨phenyl⟩ |

-continued

| | Col. I | Col. II | Col. III | | | | |
|---|---|---|---|---|---|---|---|
| | (piperazine-naphthalimide with A-N linker, R1 at 7,8; R2 at 5,6) | Cl-C(O)-X | (acylated piperazine-naphthalimide) | | | | |
| | | | | R1 | | R2 | |
| Ex. | A | | | 7 | 8 | 5 | 6 | X |

| Ex. | A | 7 | 8 | 5 | 6 | X |
|---|---|---|---|---|---|---|
| 26 | ―(CH₂)₄― | H | H | H | H | ―(CH₂)₂―C₆H₅ |
| 27 | ―(CH₂)₆― | H | H | H | H | ―CH₂―C₆H₄―CH₃ |
| 28 | ―(CH₂)₆― | H | H | H | H | ―C₂H₅ |
| 29 | ―CH―CH₂― (CH₃) | H | H | H | H | ―C₆H₃Cl₂ (2,4-dichlorophenyl) |
| 30 | ―CH₂―CH(CH₃)―CH₂― | H | H | H | H | ―CH(C₂H₅)₂ |
| 31 | ―CH(CH₃)―CH(CH₃)―CH₂― | CF₃ | H | H | H | ―C₆H₄―F |
| 32 | ―(CH₂)₂― | Cl | H | H | H | ―t-C₄H₉ |
| 33 | ―(CH₂)₃― | H | ―CH₃ | H | H | ―CH₂―C₆H₄―OCH₃ |
| 34 | ―(CH₂)₄― | ―OCH₃ | H | H | H | ―CH(CH₃)₂ |
| 35 | ―CH(CH₃)―CH₂― | ―NO₂ | H | H | H | ―(CH₂)₂―C₆H₄―Br |
| 36 | ―CH₂―CH(CH₃)―CH₂― | ―CN | H | H | H | ―C₆H₃(CH₃)₂ |
| 37 | ―(CH₂)₂― | Cl | H | H | Cl | ―C₆H₅ |
| 38 | ―(CH₂)₃― | H | Br | H | H | ―CH₂―C₆H₄―NO₂ |
| 39 | ―(CH₂)₄― | t-C₄H₉ | H | H | H | ―CH₂―C₆H₅ |
| 40 | ―(CH₂)₂― | H | ―OC₂H₅ | H | H | ―CH₃ |

-continued

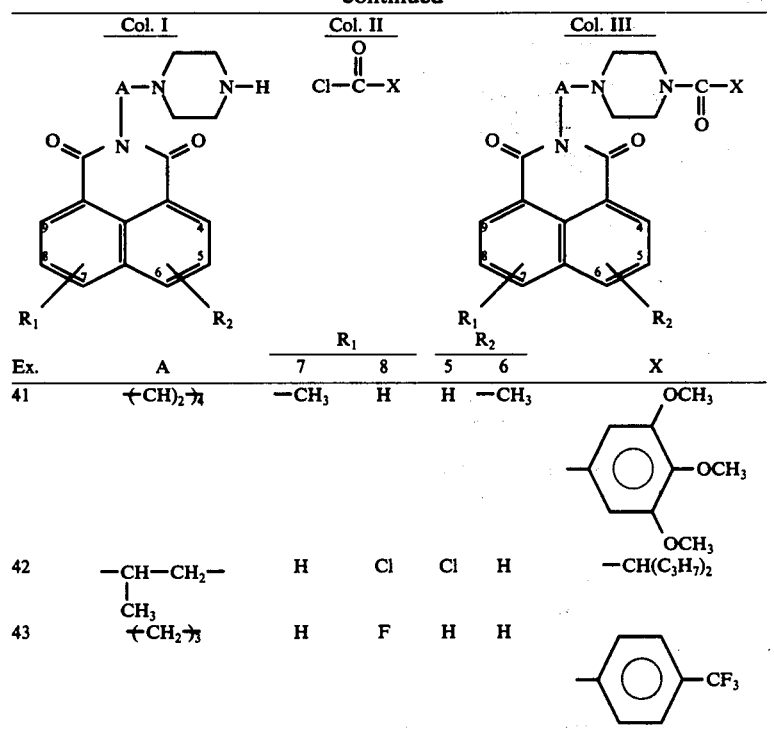

| Ex. | A | R₁ 7 | R₁ 8 | R₂ 5 | R₂ 6 | X |
|---|---|---|---|---|---|---|
| 41 | ─(CH₂)₄─ | ─CH₃ | H | H | ─CH₃ | 2,4,5-trimethoxyphenyl |
| 42 | ─CH(CH₃)─CH₂─ | H | Cl | Cl | H | ─CH(C₃H₇)₂ |
| 43 | ─(CH₂)₃─ | H | F | H | H | 4-CF₃-phenyl |

What is claimed is:

1. A compound of the formula:

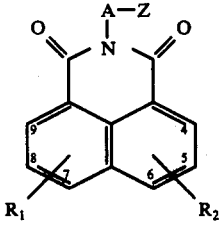

wherein Z is

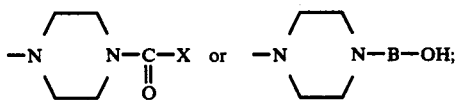

A is straight or branched chain alkylene of 2 to 6 carbons; B is straight chain alkylene of 2 to 4 carbons; X is straight or branched chain alkyl of 1 to 8 carbons, phenyl, benzyl, phenethyl, substituted phenyl, substituted benzyl or substituted phenethyl wherein said phenyl ring substituent is straight or branched chain alkyl of 1 to 4 carbons, straight or branched chain alkoxy of 1 to 4 carbons, Cl, Br, F, CF₃, nitro, di(Cl), di(Br), di(methyl), di(methoxy), or tri(methoxy); R₁ and R₂ are located at the 7 or 8 and 5 or 6 position respectively and are independently selected from the group consisting of hydrogen, straight or branched chain alkyl of 1 to 4 carbons straight or branched chain alkoxy of 1 to 4 carbons Cl, Br, F, amino, nitro, CF₃, and cyano; and a pharmaceutically acceptable acid addition salt thereof.

2. The compound of claim 1 wherein R₁ and R₂ are independently selected from the group consisting of hydrogen, methyl, methoxy, Cl, Br, and F; and A is straight or branched chain alkylene of 2 to 4 carbons.

3. The compound of claim 2 wherein Z is

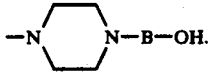

4. The compound of claim 3 wherein R₁ and R₂ are both hydrogen and A is straight chain alkylene of 2 to 4 carbons.

5. The compound of claim 4, 2-[2-[4-(2-hydroxyethyl)-1-piperazinyl]ethyl]-1H-benz[de]isoquinoline-1,3(2H)-dione, hydrochloride.

6. The compound of claim 2 wherein Z is

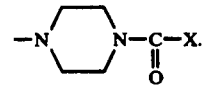

7. The compound of claim 6 wherein R₁ and R₂ are both hydrogen and A is straight chain alkylene of 2 to 4 carbons.

8. The compound of claim 7, 2-[2-[4-(3,4,5-trimethoxybenzoyl)-1-piperazinyl]ethyl]-1H-benz[de]isoquinoline-1,3(2H)-dione, hydrochloride.

9. The compound of claim 7, 2-[2-[4-(1-oxo-2-propylpentyl)-1-piperazinyl]ethyl]-1H-benz[de]isoquinoline-1,3(2H)-dione, hydrochloride.

10. A pharmaceutical composition useful for treating mammals having a protozoa infection comprising a compound or mixture of compounds of claim 1 and a pharmaceutically acceptable carrier.

11. The method of treating a mammal having a protozoa infection comprising administering an effective amount of the compound of claim 10.

* * * * *

UNITED STATES PATENT AND TRADEMARK OFFICE
CERTIFICATE OF CORRECTION

PATENT NO. : 4,070,465
DATED : January 24, 1978
INVENTOR(S) : Peter C. Wade, et al.

It is certified that error appears in the above-identified patent and that said Letters Patent are hereby corrected as shown below:

Column 9, Example 27 under the heading A the entry should read:

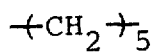

Signed and Sealed this

Twenty-ninth Day of August 1978

[SEAL]

Attest:

RUTH C. MASON
Attesting Officer

DONALD W. BANNER
Commissioner of Patents and Trademarks